United States Patent [19]

Infante

[11] 4,264,640

[45] Apr. 28, 1981

[54] METHOD FOR PREPARING A DENTAL PROSTHESIS

[76] Inventor: Samuel J. Infante, 1 Rosedale Ter., Livingston, N.J. 07039

[21] Appl. No.: 938,153

[22] Filed: Aug. 30, 1978

[51] Int. Cl.³ ............................................. A61C 13/00
[52] U.S. Cl. .......................................... 427/2; 264/20; 433/203; 433/223
[58] Field of Search ....................... 32/8, 12; 427/2, 4; 433/203, 223, 202; 264/20

[56] References Cited

U.S. PATENT DOCUMENTS

| | | | |
|---|---|---|---|
| 3,488,846 | 1/1970 | Cornell | 32/8 |
| 3,880,662 | 4/1975 | Baskalon | 32/8 |
| 4,046,732 | 9/1977 | Infante | 32/8 |
| 4,059,901 | 11/1977 | Spalted | 32/8 |
| 4,115,922 | 9/1978 | Alderman | 32/8 |

*Primary Examiner*—Sam Silverberg
*Attorney, Agent, or Firm*—Blum, Kaplan, Friedman, Silberman & Beran

[57] ABSTRACT

Two dispersant compositions are disclosed for use in the fabrication of a dental prosthesis, the compositions serving for the dispersion and deposition of an opacifier layer and a porcelain color layer over the opacifier layer. The dispersants are so formulated that only a single firing is used to produce both the opaque and porcelain bisque simultaneously, whereas prior methods required firing of the opaque layer prior to application of the porcelain color layer. A method of application to insure effective hiding of the metallic substrate, especially near the gingival portion, is disclosed.

10 Claims, No Drawings

METHOD FOR PREPARING A DENTAL PROSTHESIS

BACKGROUND OF THE INVENTION

The considerations which must be taken into account in the fabrication of a dental ceramic are presented in my U.S. Pat. No. 4,046,732 which issued on Sept. 6, 1977, and said patent is hereby incorporated by reference as if fully presented herein. As stated in said patent, the dark color of the substrate, usually a platninum alloy or stainless steel, must be masked. This is generally accomplished through the use of an opaque ceramic in the form of a base coat directly upon the metal substrate. Conventionally, this undercoat is applied to the metal from a dispersion in distilled water and must be baked to a hard condition prior to application of the porcelain body over the undercoat. In the absence of such an intervening firing, application of the porcelain body in distilled water will disturb the undercoat so that the benefit thereof is destroyed. This difficulty arises due to the fact that the dried ceramic coating reverts to the powdery state upon evaporation of the distilled water in which it is dispersed during the application thereof.

A further difficulty arises from the fact that the ceramic body shrinks during firing. As a result, the undercoat moves away from the gingival portion of the metallic substrate exposing same to view. As is evident, it is necessary that methods be provided for applying the two coatings and carrying out the firing thereof so that the entire metallic substrate is hidden from view.

The binders or dispersants taught in the aforenoted patent have proved to be effective in solving a number of the problems associated with hiding of the substrate and application of the porcelain thereover. However, the compositions presented in the present disclosure achieve the same objectives more simply and provide the firing at a lower temperature. The matter of the temperature is particularly important since the present compositions require firing at temperatures as high as 1900° F. The time required to reach this temperature is undesirably great, and, firing at such a high temperature shortens the life of the furnace appreciably. As is evident, then, it would be desirable to be able to overcome these difficulties, both for the purpose of achieving a superior product and for decreasing the cost of manufacture.

SUMMARY OF THE INVENTION

A dispersant suitable for preparation of a base layer of ceramic opaque on a dental prosthesis includes a styrenebutylacrylate-acrylic acid terpolymer, a styrene-methylmethacrylate-methacrylic acid terpolymer and a copolymer of ethyl acrylate and acrylic acid, all of which polymers are preferably neutralized with ammonia. In view of the high fusion point of the ceramic opaque to be suspended in said dispersant it is desirable that a small quantity of borosilicate glass powder be added to the dispersant.

A dispersant for a finish coat in which porcelain to match both the gingival and incisal tooth surfaces is to be suspended comprises polyvinyl alcohol and a copolymer of methylmethacrylate and vinyl acetate in aqueous methanol. This finish coat is compatible with the base layer in that, once the base layer has dried, the finish coat may be applied without damage to the base layer.

Where it is desired to slow down the rate of drying of the finish coat to facilitate shaping same, aqueous isopropanol may be added.

The above dispersants are readily dried by the use of hot air, for instance, and no firing is required prior to deposition of the finish porcelain coat. Generally, a first firing at 1770° F. to produce a bisque and a second firing at about 1800° F. to produce the final glaze will suffice. The final adjustment of the prosthesis, as by grinding, for instance, is carried out on the prosthesis in the bisque state. The damage to the finish is then effected by the second firing to produce a glaze. In the absence of a flux such as borosilicate glass in the ceramic opaque coating, the bisque firing must be carried out at about 1900° F. The presence of the powdered glass makes it possible to reduce the temperature of the two firings to the values given above.

To prevent exposure of the gingival portion of the prothesis as a result of shrinkage during firing, the ceramic opaque coating should be scraped away from this region after the bisque firing. The porcelain coating should then be applied so that it covers both the ceramic opaque coating and the gingival portion of the prosthesis. The porcelain coating will adhere strongly to the metallic substrate so that it will not be exposed during the second firing.

Accordingly, an object of the present invention is a base coat dispersant for dispersing a ceramic opaque in the preparation of an undercoat on a substrate in the manufacture of a dental prosthesis.

Another object of the present invention is a second dispersant for dispersing porcelain color in the preparation of a finish coat in the manufacture of a dental prosthesis.

A further object of the present invention is a pair of compositions to be used in the manufacture of a dental prosthesis wherein only two firings are necessary.

An important object of the present invention is a pair of compositions for use in the preparation of a dental ceramic in the manufacture of a dental prosthesis where the firing of said dental ceramic need be carried out at a temperature of only about 1800° F.

A significant object of the present invention is an improved method of preparing a dental prosthesis.

Yet another object of the invention is a dispersant for lowering the firing temperature of an opaque ceramic base coat by incorporation of a glass flux in said dispersant.

Another important object of the invention is a method of preparing a ceramic coating over a dental prosthesis base to produce a coating which covers the gingival margin of said prosthesis.

Still other objects and advantages of the invention will in part be obvious and will in part be apparent from the specification.

The invention accordingly comprises compositions of matter possessing the characteristics, properties and the relation of constituents which will be exemplified in the compositions hereinafter described, and the several steps by which said compositions are utilized and the scope of the invention will be indicated in the claims.

DETAILED DESCRIPTION OF THE PREFERRED EMBODIMENTS

As aforenoted, in the preparation of a dental ceramic in which a color opaque, generally of porcelain, forms an undercoat for hiding the metal of the prosthesis and a finish coat comprises color porcelains for matching the gingival and incisal surfaces of the remaining teeth in the mouth, dispersants containing binders may be used for preparation of each of the coats as disclosed in my patent. The binders taught herein make it possible to prepare each of the coats in one or more layers as desired, the binders being compatible with each other and with themselves. In other words, a layer may be deposited and then dried, and if it is determined that the thickness should be increased or otherwise modified, an additional layer can be deposited over an earlier layer of the same dispersant for purposes of shaping or increasing the depth of the ceramic opaque or of the porcelain. In addition, a finish coat can be deposited over a base coat without lifting same. The following Examples will clarify both the compositions which provide for complete flexibility in the preparation of dental prostheses and the method of preparing same.

CERAMIC OPAQUE DISPERSANT—EXAMPLE 1

|  | Range | Preferred Range |
|---|---|---|
| 25 parts solution A | 20–30 parts | 23–27 parts |
| 25 parts solution B | 20–30 parts | 23–27 parts |
| 50 parts 0.85% ammonia | 40–60 parts of 0.75–0.95% ammonia | 46–54 parts of 0.82–0.88% ammonia, | all parts by volume.

Solution A is an aqueous solution containing 19–25% weight % of a copolymer of 93–97 parts by volume ethyl acrylate and 3–7 parts by volume of acrylic acid.

Solution B comprises 60–66% weight % water, 20–24 weight % of a terpolymer comprising approximately 10 weight % styrene, 85 weight % butylacrylate and 5 weight % acrylic acid, and 13–17 weight % of a second terpolymer comprising approximately 5 weight % methacrylic acid, both terpolymers preferably being neutralized with ammonia. The acrylic acid and methacrylic acid contents of the terpolymers must be large enough to provide the necessary solubility. The firing temperature of the above composition is about 1900° F., whether to produce a bisque or a glaze.

In depositing the composition containing ceramic opaque suspended in the dispersant of Example 1, it is desirable to coat the metal substrate with a composition containing only a minor amount of the ceramic opaque in order to produce good adhesion to the metal. The hot air from a 1200 or 1800 watt hair dryer may conveniently be used for drying this underlayer, the drying process generally taking about one minute. A second layer can then be deposited using a spatula, the composition for the second coat preferably being thicker. This may be patted onto a thickness of up to about one mm thickness. This layer can then be dried by the same technique, the drying process taking from 5 to 7 minutes. Since the coat contains a polyacrylate resin, it has sufficient resistance to water so that the finish coat containing porcelain may be applied without danger of lifting the base coat.

As is well known, ceramic opaque has a relatively high fusion temperature; consequently, the firing time is undesirably long and the firing temperature is sufficiently high so that the life of the furnace used for firing the product is undesirably short. The fusion temperature can be lowered by the inclusion of a small quantity of borosilicate glass in the dispersant. The following composition results in a base coat having a firing temperature of about 1800° F.

EXAMPLE 2

|  | Range |
|---|---|
| 25 parts solution A | 20–30 parts by volume |
| 25 parts solution B | 20–30 parts by volume |
| 50 parts 0.85% ammonia | 40–60 parts by volume |
| 0.4 parts borosilicate glass powder | 0.3–0.5 parts by weight per 100 parts solution. |

The finish coat in the final prosthesis must satisfy requirements as to color and as to shape. Moreover, the color of the remaining teeth in the mouth generally varies between the gingival and incisor surfaces. Accordingly, the dispersant for the finish coat must make it possible to adapt both the shape and the color of the finished prosthesis to the teeth in the mouth. The following dispersant for the finish coat can be deposited in as many layers as is desired and can readily be shaped by the standard techniques well known to dental technicians.

PORCELAIN DISPERSANT—EXAMPLE 3

|  | Range | Preferred Range |
|---|---|---|
| 10 parts Solution C | 8–12 | 9.5–10.5 |
| 17 parts polyvinyl alcohol | 6–8 | 6.5–7.5 |
| 833 parts water | 800–865 | 910–955 |
| 150 parts methanol | 130–175 | 145–155 |

All parts by volume.

Solution C comprises 63–67 weight % of a copolymer of 88–91 weight % methylmethacrylate, 9–12 weight % vinyl acetate, with the remainder being water. A minor quantity of 1,3-butanediol may be added to increase the solubility of the copolymer.

The porcelain dispersant of Example 3 dries relatively rapidly. Accordingly, where the dental technician desires a composition which dries more slowly, thus providing more time for shaping, water and isopropanol or denatured ethyl alcohol may be added to slow the drying rate. A suitable composition is shown in the following example:

EXAMPLE 4

1000 parts of the dispersant of Example 3
90–110 parts water
350–450 parts isopropanol
All parts by volume.

In general, the temperature of each of the layers or coats should be raised to at least 250° F. and may be raised as high as 450° F. before applying the next layer or coat. Thorough drying in this way contributes to rendering each layer or coat impervious to attack by the next layer or coat. Also, as aforenoted, a first firing at 1775° F. (if flux is present in the composition) to form a bisque and a second firing at 1800° F. to produce the finished product results in a product with good adhesion, high strength and excellent appearance. Also, firing time is greatly reduced and the life of the furnace used for carrying out firing is substantially increased. In the absence of flux such as borosilicate the firing temperature must be about 1900° F.

It has been found that all porcelains, on baking and firing, shrink considerably and will pull up and away from the metal base at the gum line, i.e., the gingival portion, disclosing bare metal. The labial or front sections of the bridge have a feathery edge and have no collar. The dried film of dental opaque should be scraped away so that metal is disclosed at the feathery thin edge that continues into the gum. This base edge of metal will accept and hold the virgin porcelain placed over the opaqued film.

It will thus be seen that the objects set forth above, among those made apparent from the preceding description, are efficiently attained and, since certain changes may be made in the above composition of matter and process without departing from the spirit and scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A method of preparing a dental prosthesis, comprising coating a metal base with a ceramic opaque coat dispersed in a first organic binder, drying the coat, scraping away said coat at the gum line to expose said metal base, coating the dried ceramic opaque coat and exposed base at the gum line with a porcelain coat dispersed in a second organic binder, drying and firing the prosthesis.

2. The method of preparing a dental prosthesis of claim 1, comprising the steps of adding flux to said ceramic opaque coat prior to applying same, adjusting said porcelain coat after the first firing and carrying out a second firing to produce a glaze, said first firing being effected at about 1770° F. and said second firing being effected at about 1800° F.

3. The method of claim 1, including the step of dispersing a ceramic opaque in the first organic binder, which comprises a solution of a copolymer of ethyl acrylate and acrylic acid neutralized with ammonia and a solution of a first terpolymer of styrene, butylacrylate and acrylic acid and a second terpolymer of styrene, methylmethacrylate and methacrylic acid, both of said terpolymers being neutralized with ammonia and dilute ammonia, the acid contents of said copolymer and terpolymers being great enough to provide aqueous solubility.

4. The method of claim 3, further including the step of preparing said first organic binder by mixing from about 20 to 30 parts by volume of said copolymer solution, 20 to 30 parts by volume of said terpolymer solution and 40 to 60 parts by volume of about 0.65 to 0.95 weight percent dilute aqueous ammonia.

5. The method of claim 4, further comprising the step of including from about 0.3 to 0.5 weight percent powdered borosilicate glass in said first organic binder for lowering the firing temperature of the dispersant.

6. The method of claim 3, including forming the copolymer solution by mixing an aqueous solution of about 19 to 25 weight percent copolymer of about 93 to 97 parts by volume ethyl acrylate and 3 to 7 parts by volume acrylic acid and forming the aqueous terpolymer solution by mixing an aqueous solution of about 20 to 24 weight percent of the first terpolymer of about 10 weight percent styrene, 85 weight percent butylacrylate and 5 weight percent acrylic acid and an aqueous solution of 13 to 17 weight percent of the second terpolymer of about 10 weight percent styrene, 85 weight percent methylmethacrylate and 5 weight percent methacrylic acid.

7. The method of claim 1, including the step of forming the second organic binder by mixing an aqueous solution of a copolymer of methylmethacrylic and vinyl acetate with polyvinylalcohol and methanol.

8. The method of claim 7, wherein said second organic binder comprises from about 8 to 12 parts by volume of copolymer of about 88 to 91 weight percent methylmethacrylate and 9 to 12 weight percent vinylacetate, from about 6 to 8 parts by volume polyvinylalcohol, from about 800 to 865 parts by volume water and from about 130 to 170 parts by volume methanol.

9. The method of claim 8, further including from about 90 to 112 parts by volume water and 350 to 450 parts by volume isopropanol.

10. The method of claim 7, further including the step of adding an effective amount of 1,3-butanediol for increasing the solubility of the copolymer.

* * * * *